(12) United States Patent
Lorincz

(10) Patent No.: US 6,239,906 B1
(45) Date of Patent: May 29, 2001

(54) FLEXIBLE MICROSCOPE SLIDE

(76) Inventor: Andrew E. Lorincz, 3628 Belle Meade Way, Mountain Brook, AL (US) 35223-1508

(*) Notice: Subject to any disclaimer, the term of this patent is extended or adjusted under 35 U.S.C. 154(b) by 0 days.

(21) Appl. No.: 09/399,718

(22) Filed: Sep. 21, 1999

Related U.S. Application Data

(60) Continuation-in-part of application No. 09/122,984, filed on Jul. 27, 1998, now abandoned, which is a division of application No. 08/929,234, filed on Sep. 4, 1997, now Pat. No. 5,812,312.

(51) Int. Cl.⁷ .................................................. G02B 21/34
(52) U.S. Cl. ............................................ 359/396; 356/244
(58) Field of Search .................................. 359/396, 397, 359/398; 356/244

(56) References Cited

U.S. PATENT DOCUMENTS

| | | |
|---|---|---|
| 3,532,412 | 10/1970 | Miller . |
| 3,551,023 | 12/1970 | Brackett . |
| 3,556,633 | 1/1971 | Mutschmann et al. . |
| 3,764,215 | 10/1973 | Wallach . |
| 3,930,928 | 1/1976 | Tapert . |
| 4,101,980 * | 7/1978 | Stepan et al. ........................ 2/9 |
| 4,171,866 | 10/1979 | Tolles . |
| 4,188,246 | 2/1980 | Lipshaw . |
| 4,302,480 | 11/1981 | Fischer et al. . |
| 4,545,831 | 10/1985 | Ornstein . |
| 4,635,790 | 1/1987 | Jackson et al. . |
| 4,935,374 | 6/1990 | Jacobs et al. . |
| 5,202,230 | 4/1993 | Kamentsky . |
| 5,364,790 | 11/1994 | Atwood et al. . |
| 5,365,615 * | 11/1994 | Piszkin ............................. 2/422 |

FOREIGN PATENT DOCUMENTS 2163866  3/1986 (GB) .

OTHER PUBLICATIONS

Lorincz et al., Supravital Microscope Fluorescence Technique Used to Identify Spirochetes. *Annals of Clinical and Laboratory Science,* 19: 313–314 (1989).

Lorincz, Andrew E., One Step On–Site Epi–Fluorescence Detection of Fungi: A Possible Alternative to KOH Screening. *Annals of Clinical and Laboratory Science,* 23: 307 (1993).

Lorincz, Andrew E., Direct Visualization of Mycoplasma via Supravital Staining and Fluorescence Microscopy. *Israel J. of Med,* 5: 543 (1987).

Lorincz, Andrew E., Rapid Method for the Identification of Mycoplasma Organisms. *Manual of Procedures for the Application of Nucleic Acid Probes and Monoclonal Antibodies and Human Disease,* pp. 163–165 (1987).

Hiraoka et al., Diagnosis of urinary tract infection by urine microscopy using a disposable counting chamber. *Scand J. Clin Lab Invest.,* 53: 705–709 (1993).

Petcharuttana et al., Fluorescence microscopy of DES–induced morphologic transformation in unfixed, cultured cells, *J. Oral Pathol Med.* 18: 451–456 (1989).

* cited by examiner

*Primary Examiner*—Jon Henry
(74) *Attorney, Agent, or Firm*—Kenneth M. Bush, Esq

(57) ABSTRACT

A flexible plastic microscope slide which can be folded over such that a viewing portion of the slide can be placed against a specimen to obtain a sample directly therefrom without the need of transferring devices, thereby reducing biological hazards. The slide is designed for on-site collection, staining, and viewing of cells in biological fluid and tissue samples, preferably with an epi-fluorescence microscope. This novel slide permits point-of-care screening in a matter of minutes of any biological fluid or tissue sample for presence of infectious agents.

18 Claims, 3 Drawing Sheets

90°

11

150°

11

FLEXIBLE MICROSCOPE SLIDE

RELATED PATENTS

This application is a continuation-in-part of U.S. patent application Ser. No. 09/122,984, filed on Jul. 27, 1998, now abandoned, which is a divisional application of U.S. patent application Ser. No. 08/929,234, filed on Sep. 4, 1997, now U.S. Pat. No. 5,812,312.

FIELD OF THE INVENTION

The present invention relates to microscope slides. More particularly, the present invention relates to a flexible microscope slide capable of being folded over such that a viewing area of the slide can be placed against a specimen to obtain a sample directly therefrom without the need of transferring devices, after which, the slide will return to its original shape for viewing under a microscope.

BACKGROUND OF THE INVENTION

Presently used methods for analyzing biological specimens for cellular dysmorphology and microbial infection are both time consuming and costly. For example, tissue samples taken from patients, such as needle biopsies and aspirates, typically must be chemically fixed and stained, and oftentimes sectioned, and then prepared on microscope slides before they can be examined.

Additionally, in many circumstances, biological samples must first be cultured before the processing steps mentioned above. Another problem concerns the resulting specimen itself, which is usually substantially altered by fixation and fragmentation during the preparation process.

Another problem concerns unnecessary procedures, which again waste time and resources.

In a typical urinalysis, for example, a sample is obtained from a patient and subjected to a "dipstick" screening procedure. Light microscopic examination of the sediment following centrifugation of the urine specimen is then performed. If there are any abnormal results from these examinations, the sample is transferred to a laboratory for microbiological culture and antibiotic sensitivity studies, which typically take from 24 to 48 hours, or longer, to obtain the results. However, in many instances as much as 80% of the urine samples submitted for culture and sensitivity studies do not result in the detection of clinically significant bacterial presence, thus wasting valuable technician time and laboratory material resources. Furthermore, in rural areas or third world countries, samples must typically be transported to remote locations for evaluation, which can magnify the problem due to additional time delays, plus additional transportation and handling costs.

The present invention represents a departure from standard microbial and morphologic studies in the practice of clinical medicine by modifying microscope slides to be used as screening tools for on-site determination of possible infection or presence of cellular dysmorphology. The slides of the present invention avoid the time associated with preparing traditional slide preparations and they further provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes and other microorganisms less than 1 micrometer (uM) in diameter or size, such as mycoplasma, other mollicutes, legionella, etc.

SUMMARY OF THE INVENTION

It is an object of the present invention to provide a microscope slide adapted for supravital staining of cells in a biological fluid or tissue sample.

It is another object of the present invention to provide a microscope slide adapted for immediate on-site screening of a biological fluid or tissue sample.

It is another object of the present invention to provide a microscope slide which is bendable so that the slide can be folded over such that a viewing area of the slide can be placed against a specimen to obtain a sample directly therefrom.

It is another object of the present invention to provide a microscope slide which is resilient so that the slide will return to its original shape for viewing under a microscope after the sample has been collected.

These and other objects of the present invention are accomplished through the use of a flexible plastic microscope slide which can be folded over such that a viewing area of the slide can be placed against a specimen to obtain a sample directly therefrom without the need of transferring devices or breakable glass components, thereby reducing biological hazards. The slide is designed for on-site collection, staining, and viewing of cells in biological fluid and tissue samples, preferably with an epi-fluorescence microscope. This novel slide permits point-of-care screening in a matter of minutes of any biological fluid or tissue sample (e.g. urine, blood, sputum, spinal fluid, amniotic fluid, tears, needle aspirates, semen, tissue touch preparations, plant sap, etc.) for presence of infectious agents (e.g. bacteria, including mycoplasma-sized mollicutes, spirochetes, fungi, parasites, etc.).

These and other objects and advantages of the invention will become apparent from the following detailed description of the preferred embodiment of the invention.

BRIEF DESCRIPTION OF THE DRAWINGS

A microscope slide embodying features of the invention is described in the accompanying drawings which form a portion of this disclosure and wherein.

DETAILED DESCRIPTION OF THE PREFERRED EMBODIMENT

The present application is a continuation-in-part of U.S. patent application Ser. No. 09/122,984, filed on Jul. 27, 1998, the disclosure of which is incorporated herein by reference. The present invention is a self-staining microscope slide designed for supravital staining of cells and microorganisms in a biological fluid or tissue sample, and adapted for immediate visual or instrumental examination of the stained cells. The American Heritage Dictionary of the English Language (3rd ed., 1992) defines "supravital" as relating to or capable of staining living cells after their removal from a living or recently dead organism. Thus, the present invention allows immediate, on-site staining of unfixed cells from a biological sample which can be immediately viewed for preliminary diagnosis of a plurality of conditions. Since supravital staining is incorporated in the prepared slides, the time and cost of drying, chemical fixation, and/or sectioning of specimens may be completely avoided.

Figure 1:
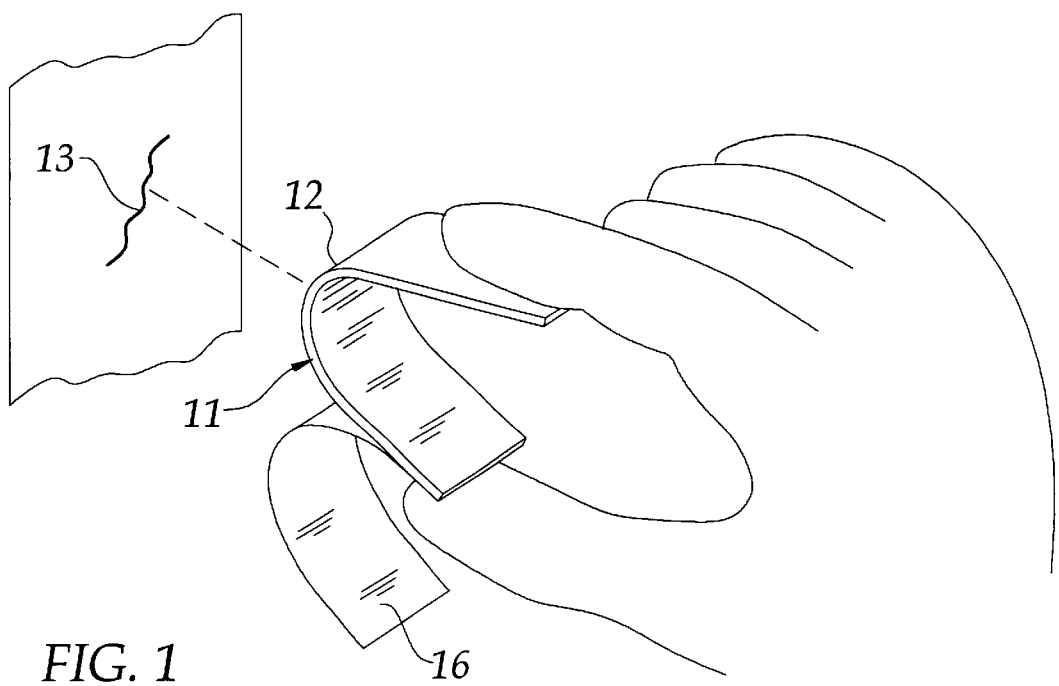
FIG. 1 perspective view of the present invention folded over for collection of a sample.
Figure 2:
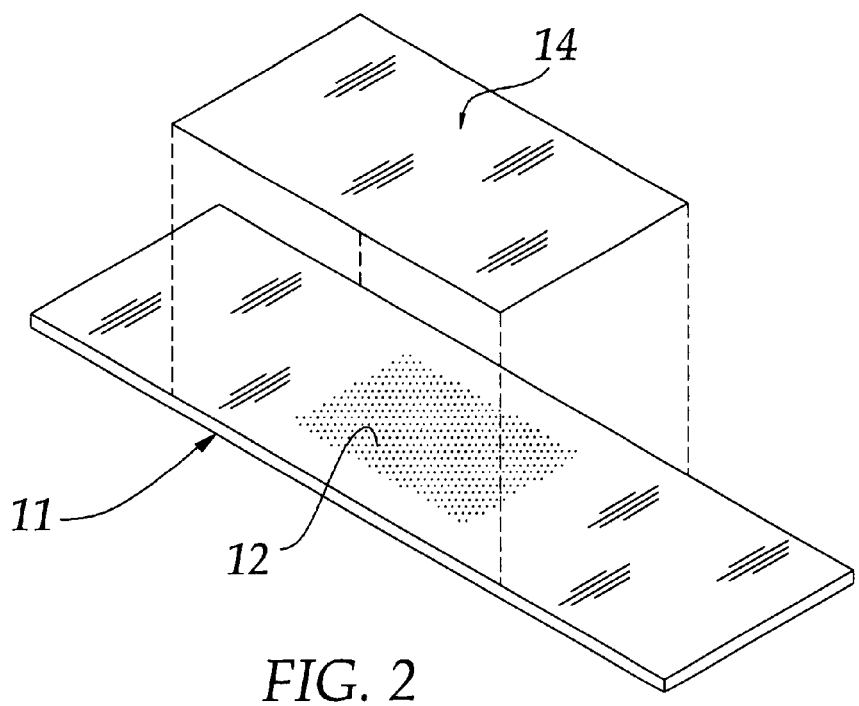
FIG. 2 is an exploded perspective view of the present invention having a rigid cover slip.
Figure 4:
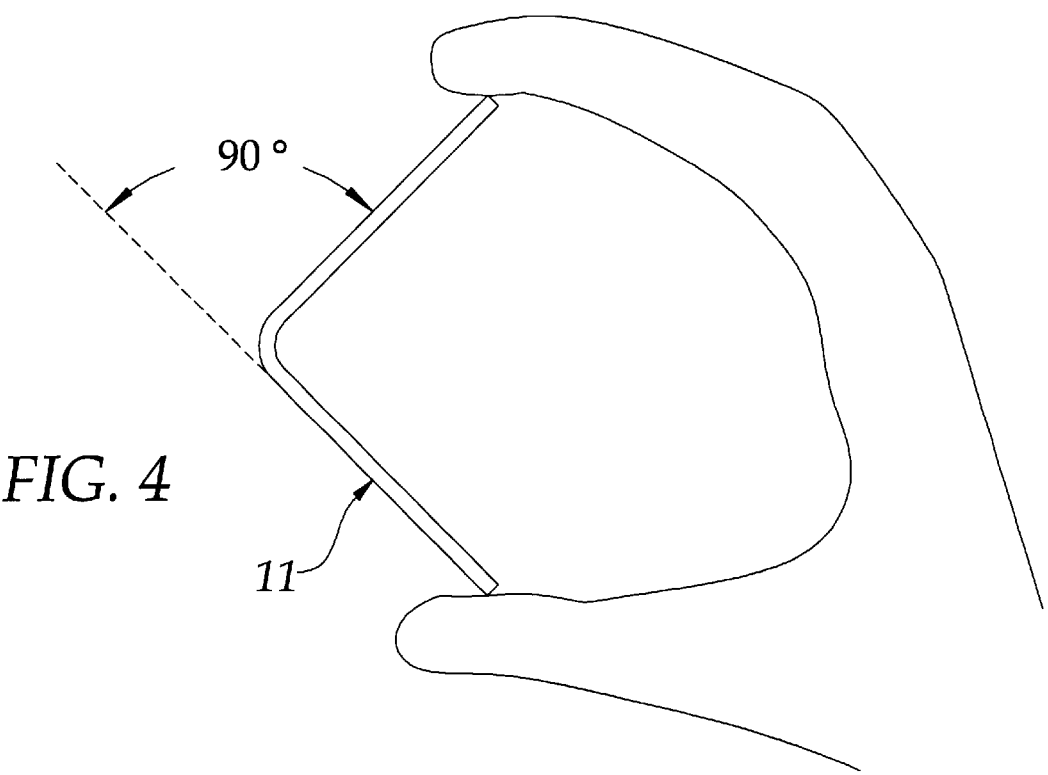
FIG. 4 is a side elevational view of the present invention folded over approximately 90 degrees.
Figure 5:
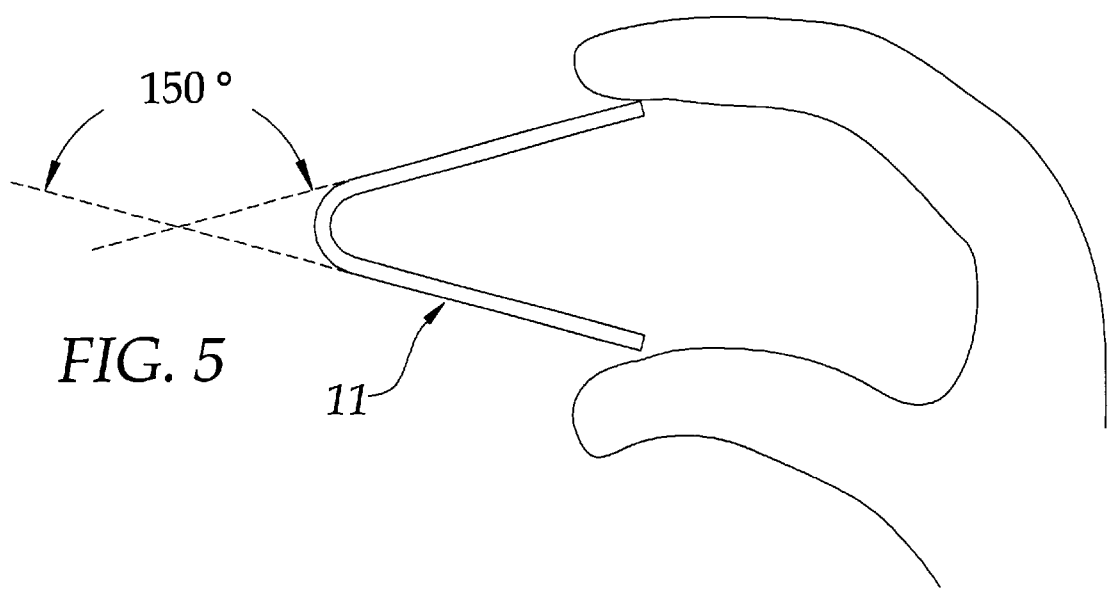
FIG. 5 is a side elevational view of the present invention folded over approximately 150 degrees.

A more complete understanding of the invention may be obtained by reference to the accompanying drawings, wherein a microscope slide 11 according to the present invention comprises a flexible plastic material, such as LEXAN® (polycarbonate) having a thickness of about 1/32 inch. As used herein, a "flexible" slide is a slide which is bendable and resilient such that the slide 11 can be folded over or bent so that a viewing area 12 can be touched directly to a specimen or suspected tissue lesion 13 (e.g. syphilitic chancre) in order to obtain a sample directly therefrom, as illustrated in FIG. 1, after which, the slide will return to its original substantially planar shape for viewing under a microscope. This removes the need for transferring means, such as a swab, and reduces the hazards and requirements for increased waste disposal of transfer equipment. The slide preferably can be folded over at least 45 degrees, and most preferably at least 90 degrees. Two perspective views of the slide folded over 90 degrees and 150 degrees are shown in FIGS. 4 and 5, respectively. While it is preferable that the slide have full resiliency such that it returns completely to its original shape, the present invention includes within its scope partial resiliency such that a slight counterbending force would be required to return the slide to its original shape.

Figure 3:
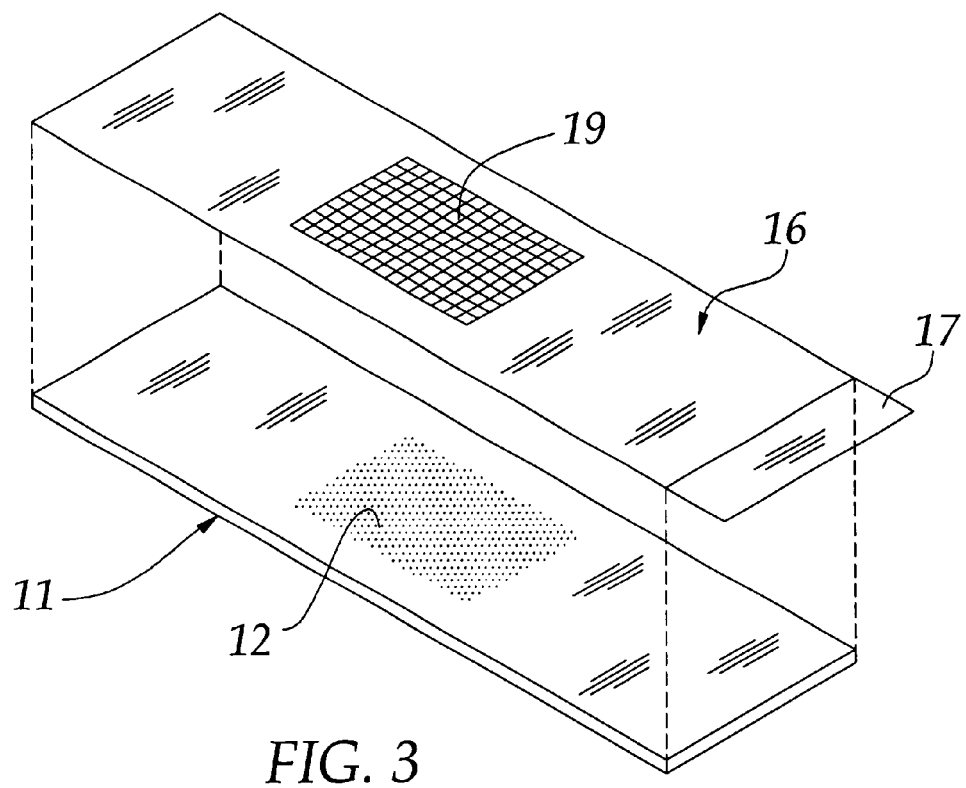
FIG. 3 is exploded perspective view of the present invention having a flexible film cover slip.

The flexible slide 11 can be transparent, opaque, or tinted. The viewing area 12 is preferably roughened and/or coated with an adhesive or hydrophilic material to promote adherence of the sample thereto. A supravital dye for staining the sample can be applied to the viewing area 12 of the slide, incorporated into the adhesive or hydrophilic material, or applied to the underside of transparent covering means, such as a rigid cover slip 14 or flexible film 16. Preferably, a flexible film 16, shown in FIG. 3, is attached to the slide 11 with a weak adhesive such that the film can be peeled back to expose the viewing area 12 for collection of the sample and replaced such that the sample intermixes with the dye, thereby staining any cells in the sample for immediate viewing under a microscope.

The flexible slide 11 is most appropriate for collecting specimens now examined by darkfield microscopy, e.g. in sexually transmitted disease clinic settings where glass slides and cover slips pose an added risk to the person collecting the specimen. The flexible slide also has the advantage of accessing difficult anatomical sites not readily reachable by a rigid slide or cover slip.

The supravital dyes are preferably water soluble fluorochromes, such as acridine orange, acridine yellow, etc., in appropriately buffered concentrations. A fluorescence or epifluorescence microscope is required to view the fluorescent stained samples, and the latter if frosted, opaque, or tinted slides are used because these particular slides can effect fluorescent light dispersion therethrough. By staining the sample with a fluorochrome and utilizing an epi fluorescent microscope for viewing, the visualization of the structures in the sample is greratly enhanced compared to visualization with phase contrast or similar light microscopy. This is analogous to viewing the moon at night compared to viewing the moon during the day. The vital dye will diffuse into a living cell or microorganism, without killing the cell, and complex with macromolecules such as DNA, glycosaminoglycans, lipopolysaccharides, etc., which are present in the cell. The dye-macromolecule complexes are rendered fluorescent and can be visualized after excitation with appropriate light frequencies from mercury lamps, halogen lamps, tungsten lamps, etc.

The film 16 comprises a flexible transparent material having an adhesive on one side, such as Scotch™ brand tapes (3M Company), for placement over the viewing surface of the slide 11 such that the adhesive surface is in contact with the viewing surface of the slide. In an alternate embodiment, the adhesive can be placed only along the margins of the film so that no adhesive overlaps the viewing area 12. The film 16 preferably has a portion 17 on at least one end having no adhesive thereon such that the portion 17 acts as a grip for handling the film 16.

Other features which are beneficial include the addition of size references, such as fluorescent microspheres (not shown) of known dimension (e.g. 1 uM), to the slide or covering means such that they coincide with the field of focus of the sample. This facilitates focusing the microscope and provides an internal reference standard for size, which is preserved for photomicrography or video image capture. Other reference standards, such as a sizing grid 19 or the like, can also be incorporated as by etching or photographic reproduction onto the surface of the slide or covering means to allow sizing and quantitation of cells, microorganisms or the like.

Since the collected biological fluid sample (e.g. blood, urine, sputum, bronchial or gastric washings, spinal fluid, synovial fluid, cervical smear, semen, prostate secretion, tears, needle biopsy specimens, amniotic fluid, plant sap, etc.) is not dried or chemically fixed, the morphology and mobility of the intact cells and/or microorganisms is maintained. Nuclear morphology of the living cells is preserved for immediate visual (or image) analysis facilitating determination of the presence or absence of malignant dysmorphology. Similarly, the presence of abnormal macromolecular "storage" in cell (e.g. in amniotic fluid, white blood cells, cultured fibroblasts) can be readily observed. Although all DNA containing cells are non-specifically stained by the fluorochrome, the size, shape and movement patterns of any microorganisms present may be helpful in serving for preliminary identification of the microorganisms. Additionally, the presence or absence of viral inclusion bodies can also be observed, which is of some consequence in examining oral and nasal smears.

Nowadays, with the availability of portable fluorescence microscopes that can even be powered by an automobile battery, the ability to use the slides can be readily adapted for field use in developing countries, rural clinics, mobile vans, etc. If visual screening confirms the presence of bacterial or fungal infection, or protozoan infestation, the same specially prepared slides that are used for on-site screening, can be used for specimen transfer. Such transfer to a peripheral or reference laboratory permits further culture as well as definitive identification via histochemical study or DNA analysis (e.g. PCR, ELISA, monoclonal antibody studies). Furthermore, photomicrographs or digital imaging techniques can permanently capture what can be visualized in the epi-fluorescence microscope. Transmission of these digital images to remote central laboratories for evaluation is also a possibility.

By utilizing the slides in the operating room, examination of biopsy tissue touch preparations or needle biopsies might obviate the need for the expensive microtomes and cytotechnicians now required for present quick-frozen tissue section studies. Turnaround times for results would also be considerably faster. The delays between specimen collection and reporting of laboratory results do not exist when testing is conducted on-site, which permits immediate action by the physician once testing is completed. Thus, this methodology should significantly improve clinical practice guidelines for physicians ordering laboratory tests. For example, an uncentrifuged, supravitally stained urine sample on the present slide can be immediately visualized with an epifluorescent microscope, allowing superior visualization of the structures in the sample to substantially increase the accuracy of diagnosing urinary tract infections. The principle and methodology are scientifically accurate, reproducible, easily taught and easily learned; even by nonprofessional laboratory technicians. The slides can also be used to examine plant specimens, such as plant sap, for microbial infections and the like.

The slides of the present invention provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes. Additionally, the slides permit detection of mycoplasma species and other mollicutes (smallest known bacteria that do not have cell walls), which cannot be visualized by standard light transmission microscopes.

Production cost should be less expensive than the cost of producing glass microscope slides and glass cover slips. Chances for breakage and infecting clinical personnel should be diminished. The weight of the slides is far less than that of glass slides or culture plates, thus facilitating transport and storage. Importantly, laboratory wastes is concomitantly reduced.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. A planar microscope slide comprising a bendable and resilient material, wherein said slide can be folded over such that a viewing portion of said slide can be placed against a specimen to collect a sample directly therefrom, after which, said slide will return to a substantially planar state for viewing under a microscope, wherein said slide can be folded over at least 45 degrees.

2. A microscope slide according to claim 1 wherein said slide can be folded over at least 60 degrees.

3. A microscope slide according to claim 1 wherein said slide can be folded over at least 90 degrees.

4. A microscope slide according to claim 1 wherein said slide can be folded over at least 120 degrees.

5. A microscope slide according to claim 1 wherein said slide can be folded over at least 150 degrees.

6. A microscope slide according to claim 1 wherein said viewing portion comprises a roughened surface to promote adherence of the sample thereto.

7. A microscope slide according to claim 1 wherein said viewing portion has a dye adhered thereto for staining the sample.

8. A microscope slide according to claim 7 wherein said dye comprises a fluorochrome.

9. A microscope slide according to claim 1 wherein said viewing portion comprises an adhesive to promote adherence of the sample thereto.

10. A microscope slide according to claim 9 wherein said adhesive has a dye mixed therewith for staining the sample.

11. A microscope slide according to claim 1 wherein said viewing portion comprises a hydrophilic material to promote adherence of the sample thereto.

12. A microscope slide according to claim 1 wherein said bendable and resilient material is polycarbonate.

13. A microscope slide according to claim 1 further comprising means for covering said viewing portion such that the collected sample is in contact with said viewing portion between said slide and said covering means.

14. A microscope slide according to claim 13 wherein said covering means has a dye adhered thereto for staining the sample.

15. A microscope slide according to claim 1 wherein said slide further comprises reference markers to assist in focusing the microscope.

16. A microscope slide according to claim 1 wherein said slide further comprises a reference standard for measuring the size and quantity of cells or microorganisms in the sample.

17. A flexible plastic microscope slide comprising a bendable, resilient material such that said slide can be folded over so that a viewing portion of said slide can be placed against a specimen to obtain a sample directly therefrom, after which, said slide will return to a substantially planar state for viewing under a microscope, wherein said slide can be folded over at least 90 degrees.

18. A flexible plastic microscope slide having first and second ends, wherein said slide comprises a bendable, resilient material such that said slide can be folded over so that a viewing portion of said slide can be placed against a specimen to obtain a sample directly therefrom, after which, said slide will return to a substantially planar state for viewing under a microscope, wherein said slide can be folded over such that said first and second ends are in abutment.

* * * * *